United States Patent [19]
Beede et al.

[11] 4,317,681
[45] Mar. 2, 1982

[54] MODIFIERS FOR ION-LEACHABLE CEMENT COMPOSITIONS

[75] Inventors: Charles H. Beede, East Brunswick; Richard N. Zirnite, Somerset, both of N.J.

[73] Assignee: Johnson & Johnson, New Brunswick, N.J.

[21] Appl. No.: 204,982

[22] Filed: Nov. 7, 1980

[51] Int. Cl.$^3$ ................................................. C09K 3/00
[52] U.S. Cl. ........................................ 106/85; 106/35; 128/87 R
[58] Field of Search ............... 106/35, 85; 260/29.69; 128/87 R

[56] References Cited

U.S. PATENT DOCUMENTS

| | | | |
|---|---|---|---|
| 4,089,830 | 5/1978 | Tezuka et al. | 106/35 |
| 4,123,416 | 10/1978 | Potter et al. | 106/35 |
| 4,209,434 | 6/1980 | Wilson et al. | 106/35 |
| 4,256,277 | 2/1981 | Maries et al. | 106/35 |

*Primary Examiner*—James Poer
*Attorney, Agent, or Firm*—Jason Lipow

[57] ABSTRACT

A cementitious composition including dry ion-leachable glass powder and further including an agent for modifying the rate of setting. The agent is selected to include the d,l form of tartaric acid.

13 Claims, 4 Drawing Figures

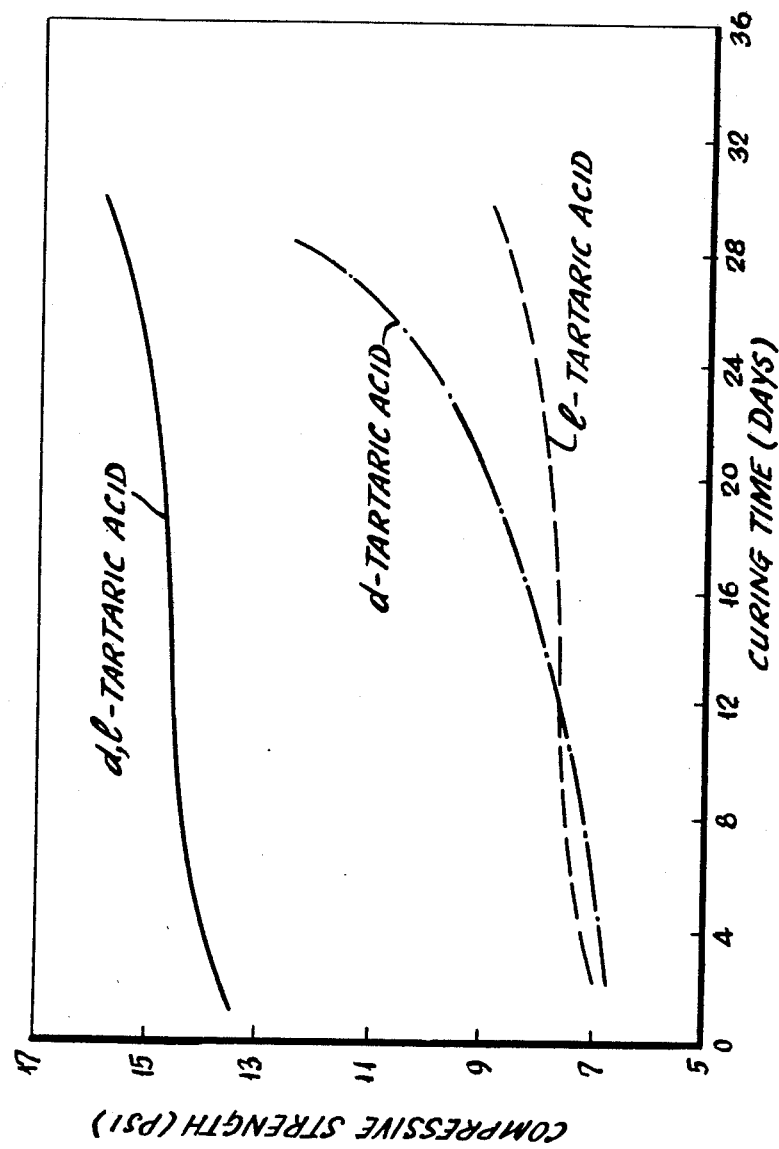

MODIFIERS FOR ION-LEACHABLE CEMENT COMPOSITIONS

BACKGROUND OF THE INVENTION

This invention relates to cement compositions comprising ion-leachable inorganic compounds preferably in the form of glasses. In particular, this invention relates to modifying the setting times associated with such cement compositions.

Ion-leachable inorganic compounds such as the oxides of aluminum, zinc, magnesium and calcium have been intermixed with other components such as silica and formed into glasses which, when combined with such hydrogen donating compounds as acids, will set up into a cementitious mass. The mechanism for the reaction has been described by Alan D. Wilson et al. (J. Dent Res. 58(3), 1065–1071, March 1979) and may be represented by the generic equation:

| MO | + | $H_2A$ | = | MA | + | $H_2O$ |
|---|---|---|---|---|---|---|
| ion-leachable inorganic compound | | Proton donating compound | | Salt Hydrogel | | |

Cements utilizing this mechanism have generally taken the form of glass powders incorporating the ion-leachable inorganic. These are reacted with liquid acid solutions such as aqueous poly(carboxylic acid) solutions to form a salt hydrogel structure which sets up into a hard mass. Such cement forming compositions have been suggested for use in applications such as dental cements and for orthopedic casts and splints. For example, a fluoroaluminosilicate glass powder has been suggested for use as the ion-leachable component for a dental cement in British Pat. No. 1,316,129. More recently, a similar composition has been suggested for use in orthopedic surgery in U.S. Pat. No. 4,143,018.

In using such compositions for orthopedic purposes, for example, certain criteria must be met. The composition, when rendered reactive, must be capable of providing sufficient "working time", i.e., sufficient time from the start of mixing the reactants to allow the doctor time to apply and mold the cast into shape before the material reaches a stage where it is no longer malleable. Generally such times should be at least about 2 minutes and preferably from 5 to 8 minutes.

At the end of the working time period, it is most desirable that the cast set to a rock-like state as quickly as possible. While most cements, even after attaining a rock-like appearance, do not reach their ultimate strength for long periods of time, the material should reach sufficient compressive strength to allow a patient to leave the doctor's office, i.e. sufficiently hard enough to preclude deformation under expected stresses. This period is referred to as the "setting time" and should be about 6 to 15 minutes after the cast is applied.

Prior workers in the field have discovered that the rate of setting, i.e., the working and setting times, can be greatly affected by the addition of certain modifying agents, alternatively referred to in the art as chelating agents, complexing agents, accelerators, or the like. (See, for example, Wilson, et al., J. Dent. Res. Vol. 55, No. 3, p. 489–495, 1976; Crisp, et al., J. Dent. Res., Vol. 55, No. 6, p. 1023–1031, 1976; and Crisp, et al., J. of Dentistry, Vol. 7, No. 4, p. 304–319, 1979). In particular, it has been reported that tartaric acid will behave in such a way as to accelerate the gelling reaction.

Unfortunately, applicants have found that when attempting to incorporate the tartaric acid taught by the prior art into a commercial form such as could be used by an orthopedist, the reported accelerating effects have not been fully realized and the results have been disappointing. Specifically, a cement is made by incorporating the dry ingredients, to wit: glass powder, poly(carboxylic acid) and the commonly available form of tartaric acid taught by the prior art. Water is added to this cement composition immediately prior to its use, as is the practice in the orthopedic field. When such procedure is followed, the results have been poor and no great acceleration in setting times have resulted. Accordingly there is a need for an improved modifying agent.

SUMMARY OF THE INVENTION

In accordance with this invention, it has been discovered that a dry mixture of ion-leachable glass powder, poly(carboxylic acid), and tartaric acid may be provided at the time of use and will produce accelerated setting times immediately upon being combined with water. Specifically, it has been discovered that this advantageous result will occur if the tartaric acid is selected to comprise the d,l-isomeric form. Prior to this discovery, compositions have been prepared using only the d- isomeric form which is the form provided by most commercial sources of tartaric acid. It has now been discovered that a dry composition incorporating either the d-tartaric acid, the l-tartaric acid or the meso-tartaric acid in the dry form does not, when water is added, set as rapidly as when a careful selection is made to utilize d,l-tartaric acid.

In a specific embodiment, the d,l-tartaric acid containing compositions of this invention comprises from about 0.05 to about 0.20 grams of d,l-tartaric acid per gram of glass powder. Preferably, this ratio is 0.06–0.10 grams of acid per gram of glass powder. In another specific example the dry compositions are adhered to a substrate and used as an orthopedic bandage which exhibits excellent working and setting times.

BRIEF DESCRIPTION OF THE DRAWINGS

FIG. 1 illustrates, in graphical representation, the improvement of this invention as it relates to the compressive strength of cements as a function of setting time at 70° F.;

DETAILED DESCRIPTION OF THE INVENTION

Figure 3:
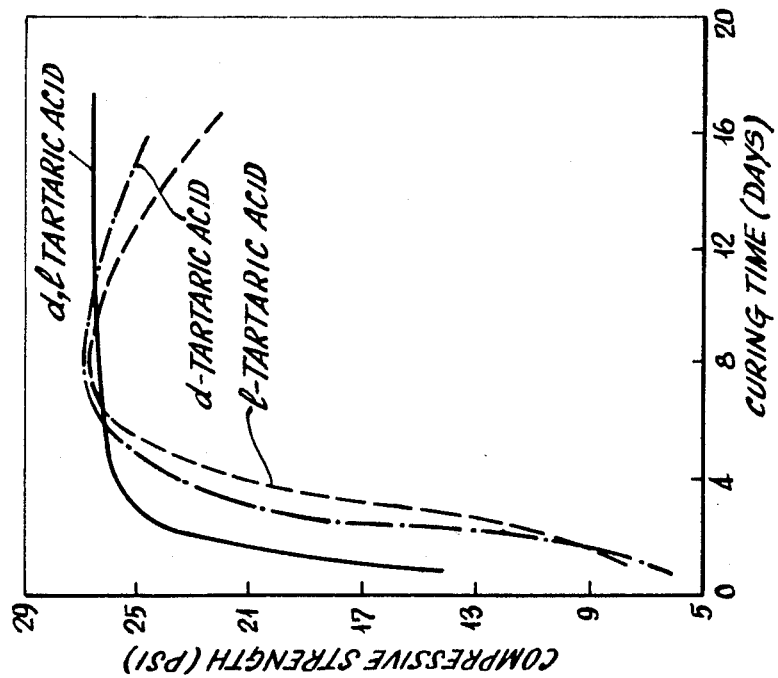
FIG. 3 is still another graphical representation, similar to FIGS. 1 and 2, at a temperature of 120° F.

The powdery cementitious mixtures of this invention comprise ion-leachable inorganic compounds, poly(carboxylic acid) and, an accelerating agent which, in accordance with the teachings of this invention is selected to comprise the d,l-isomer of tartaric acid.

The ion-leachable inorganic compounds are preferably introduced in the form of glass powders which have been formed from the oxides of alkali, alkaline earth, aluminum and zinc metals along with silica. As has been more fully discussed in a commonly assigned pending U.S. patent application filed on this same day and incorporated herein by reference, it is advantageous to provide such glass powder in as homogeneous a state as is possible and with a controlled and precise degree of crystallinity. In this aforementioned U.S. patent application, a method for realizing these criteria is described and basically comprises feeding shaped charge materials into an electric furnace, melting the materials to a molten mixture, blowing the molten mixture into thin glass fibers, and immediately quenching the fibers in a water bath. The quenched fibers are then dried and milled into the desired glass powder form.

The poly(carboxylic acid) may be one or more poly(acids) or their precursors and include polymers of monocarboxylic acids, monocarboxylic acid anhydrides, dicarboxylic acids and dicarboxylic acid anhydrides as well as interpolymers of the above or interpolymers of the above and other ethylenically unsaturated monomers. Examples of usable acids and precursors are poly(acrylic acid), itoconicacrylic acid copolymers, itoconic acid polymer, poly(arylsulfonic acids), poly(methacrylic acid) ethyl acrylate-acrylic acid copolymer, ethyl acrylate-acrylic acid copolymer and the like. Also usable are a series of poly(methyl-, vinyl-ether/maleic anhydride) copolymers sold by the GAF Corporation under the trademark "Gantrez". All of these are available as finely divided solids which may be blended with the other ingredients.

In accordance with the teachings of this invention, the accelerating agent, tartaric acid, is specifically chosen to comprise the optically neutral isomeric form and more specifically in the d,l-form (I) as distinguished from the meso form (II), to wit:

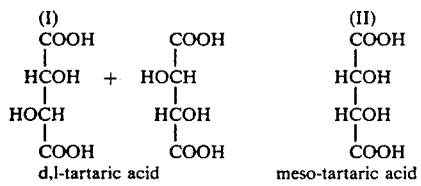

The distinction being drawn is that it has been discovered that the d,l-form, i.e., a mixture of both levo and dextro tartaric acid in a proportion so as to be optically neutral, will be effective as an accelerator in the cement compositons of this invention. On the other hand, meso-tartaric acid, a compound which in itself is chemically structured so as to be optically neutral, does not produce the desirable accelerating effect in cement compositions. Further, the commonly available dextro form and less commonly available levo form, by themselves, fail to give the desired result.

It should be understood that while the mixture of d- and l,-tartaric acid which results in absolute optical neutrality is the effective proportion of these isomers, the effect is not lost by having an excess of either of the isomers present in the tartaric acid employed and the advantages accrued by such a mixture are still substantial although only somewhat diminished. For example optimum results occur when using a mixture of 50% by weight of d-tartaric acid and 50% by weight of l-tartaric acid, the racemic proportions for tartaric acid. However, a mixture which can be thought of as a combination of 50% of racemic mixture and 50% excess d- or l-isomer (i.e., 25% d- and 75% l- or 75% d- and 25% l-) will show substantial improvement in accelerating the setting of the cementitious compositions as contrasted with prior art teachings which employ only the d- or only the l- form. Thus, a composite containing tartaric acid in which the tartaric acid comprises the racemic mixture, either alone or with an excess of either of the isomeric forms, is effective.

It should be noted that the optical isomerization of tartaric acid had been considered and discussed by prior workers and specifically in the aforementioned J. of Dentistry article (Vol. 7, No. 4, p. 304–319, 1979 Crisp et al.). These investigators, however, reached a conclusion totally contrary to that disclosed herein. In the aforementioned 1979 Crisp et al. article, aqueous solutions of polyacid and water were variously combined with either d-tartaric, l-tartaric, meso-tartaric or d,l-tartaric acids. This acidic aqueous solution was then combined with ion-leachable glass powders to form a settable cementitious mass and setting times were measured. It was concluded that the optically active isomers, i.e., d- and l-tartaric acid as well as the optically inactive racemic mixture, d,l-tartaric acid, were equally effective as accelerators. On the other hand, the meso-isomer was not effective.

The work of Crisp et al. notwithstanding, it has now been discovered that when attempting to apply these teachings to a commercial embodiment, contrary results occur and the meso-, d- and l-forms are all ineffective with only tartaric acid comprising the d,l-form providing significant acceleration. While these results are not clearly understood and may at first appear anomalous, it is clear that whereas prior experimenters were employing aqueous solutions of polyacid and tartaric acid to which the glass powder was added, the commercial embodiment taught herein employs essentially dry mixtures of solid poly(acid, tartaric acid and glass powder to which water is added at the time of use. For example, when the material is used as a dental cement, the dry powder is only combined with water at the time of use and immediately begins to set up and harden. When used as an orthopedic cast or splint, the dry powder is generally adhered to a bandage substrate such as gauze or the like. Immediately before use, the bandage is immersed in water and applied. The acceleration effect, for these commercial embodiments must accure at the time of water addition to be of practical advantage.

Upon consideration of these differences between the work of prior experimenters and the embodiment taught herein, it is hypothesized that when the prior experimenters began with either the l- or d-form of tartaric acid and formed an aqueous acid solution therewith, the solution upon standing reverted to the d,l- or racemic form. This property of d- and l- tartaric acid in aqueous acid solution is known. Accordingly, it is hypothesized that irrespective of which optical isomer the experimenter employed as a starting material, the cementitious mixture subsequently formed involved only d,l,- tartaric acid as the accelerator and hence explained the anomaly, i.e., that these experimenters concluded that the d-, l-, and d,l-forms were all equally effective.

In contrast to the work of the prior experiments, when the dry ingredients are intermixed and all first contacted with water, without first forming a precursor acid-accelerator solution, the ability to form racemic mixtures is greatly inhibited. For example, if the dry mixture employs d-tartaric acid as the accelerator, combined in dry form with solid poly(carboxylic acid) and glass powder, upon the addition of water, the mixture begins to set up immediately and probably long before there is any time for the racemic mixture to form. It is hypothesized that this is the reason that, in the commerical embodiment of this invention and contrary to the prior teachings, it is only when the d,l,-tartaric acid is present in the starting tartaric acid that any acceleration occurs.

It becomes apparent then, that what is meant by an essentially dry powder mixture as used herein, is a mixture having an insufficient amount of water to set up as a gel and hence a mixture which may be stored until use. It is implicit in the above that the amount of water is also insufficient to racemize either the d, or l-form of tartaric acid.

The following examples are given to illustrate the advantages of this invention.

The dry components, i.e., the glass, the poly(acid) and various isomeric forms of tartaric acid, are combined in various combination and proportions to form the substantially homogeneous powder compositions defined in Table 1, below. The powder compositions are mixed with water, in the proportions shown in the table to form a moldable paste. The paste is then quickly packed into a 0.635 cm. diameter by 1.27 cm. long cavity bored through the center of a 1.27 cm. thick circular Teflon mold. The filled molds are placed between glass plates weighted down by a 200 gram weight, and allowed to cure for 72 hours at 70° F. to form cylindrical pellets. The pellets are then removed from the mold and tested in an Instron Tester, operating at a head speed of 0.05 cm. per minute, to determine the compressive strength which is reported in Table I, below, in kg. per square cm.

TABLE 1

| | CEMENT COMPOSITION (POWDER) | | | | | | WATER ADDITION | COMPRESSIVE STRENGTH |
|---|---|---|---|---|---|---|---|---|
| | GLASS | | POLY(ACID) | | TARTARIC ACID | | | |
| SAMPLE | TYPE | PARTS* | TYPE | PARTS* | ISOMER | PARTS* | (ml H$_2$O/gm Powder) | (kg./cm$^2$) |
| 1 | A | 3 | A | 1 | d- | 0.49 | 0.2 | 466.8 |
| 2 | A | 3 | A | 1 | d,l- | 0.49 | 0.2 | 878.6 |
| 3 | A | 3 | A | 1 | l- | 0.49 | 0.2 | 495.5 |
| 4 | A | 3 | A | 1 | d,l- | 0.49 | 0.2 | 966.0 |
| 5 | A | 8.33 | A | 1 | d- | 0.5 | 0.25 | 252.7 |
| 6 | A | 8.33 | A | 1 | d,l- | 0.5 | 0.25 | 448.8 |
| 7 | A | 3 | B | 1 | d- | 0.3 | 0.20 | 530.0 |
| 8 | A | 3 | B | 1 | l- | 0.3 | 0.20 | 519.7 |
| 9 | A | 3 | B | 1 | d,l- | 0.3 | 0.20 | 919.7 |
| 10 | A | 3 | A | 1 | l- | 0.25 | 0.20 | 630.8 |
| 11 | A | 3 | A | 1 | d,l- | 0.25 | 0.20 | 803.8 |
| 12 | B | 3 | B | 1 | d- | 0.5 | 0.20 | 505.2 |
| 13 | B | 3 | B | 1 | d,l- | 0.5 | 0.20 | 810.6 |

*by weight

EXAMPLE 1

A series of samples are prepared consisting of a powdery mixture of ground ion-leachable glass, poly(acrylic acid), and various isomeric forms of tartaric acid. The powdered glass ingredient is made by the procedure described in the above referred to, commonly assigned, U.S. patent application filed on this day by Smyth and variously employs the following formulations:

| Glass | COMPONENT (molar parts) | | |
|---|---|---|---|
| Type | SiO$_2$ | Al$_2$O$_3$ | CaO |
| A | 4 | 2.5 | 3.5 |
| B | 4 | 2.0 | 4.0 |
| C | 4 | 2.5 | 3.5 |

The poly(acrylic acid) component is employed in forms having the following chemical characteristics:

| POLY(ACID) TYPE | Molecular Weight | Equivalent Weight |
|---|---|---|
| A | 125,000 | 79.2 |
| B | 169,600 | 80.9 |
| C | 149,000 | 77.3 |

As can be clearly evidenced from the above Table 1, cement cylinders, for which all other variables are held constant exhibit far greater compressive strengths when the accelerating form of tartaric acid is the d,l- isomer as contrasted with either the d- or l- isomer.

Thus, for example, samples 1–4 are cement for which all other variables have been held constant. For this group, those cements employing the d,l-form are almost twice as strong as those employing either of the other two isomers. Similar results are obtained for samples 5 and 6 wherein a high proportion of glass to poly(acid) is employed. Samples 7–9 also show the advantage of using the d,l-form for compositions in which the chemical properties of the poly(acid) is varied and for which a lesser amount of tartaric acid is employed. Samples 12 and 13 show the same advantageous result for the d,l-form for compositions employing a different glass formulation. Finally, samples 10 and 11, while showing substantial advantage for the d,l form over the l-form, illustrate that this advantage is somewhat diminished at lower concentrations of tartaric acid.

TABLE 2

| | CEMENT COMPOSITION (POWDER) | | | | | | WATER ADDITION | WORKING TIME | CURE TIME |
|---|---|---|---|---|---|---|---|---|---|
| | GLASS | | POLY(ACID) | | TARTARIC ACID | | | | |
| SAMPLE | TYPE | PARTS* | TYPE | PARTS* | ISOMER | PARTS* | ml H$_2$O/gm Powder | (Min.:Sec.) | (Min.:Sec.) |
| 14 | C | 100 | C | 12 | d,l- | 5 | 0.17 | 1:0 | 4:00 |
| 15 | C | 100 | C | 12 | d- | 5 | 0.17 | 1:0 | 9:30 |
| 16 | C | 100 | C | 12 | l- | 5 | 0.17 | 1:0 | 10:00 |
| 17 | C | 100 | C | 12 | meso- | 5 | 0.17 | 1:0 | 36:00 |

TABLE 2-continued

| | CEMENT COMPOSITION (POWDER) | | | | | | WATER ADDITION | WORKING TIME | CURE TIME |
|---|---|---|---|---|---|---|---|---|---|
| | GLASS | | POLY(ACID) | | TARTARIC ACID | | | | |
| SAMPLE | TYPE | PARTS* | TYPE | PARTS* | ISOMER | PARTS* | ml H$_2$O/gm Powder | (Min.:Sec.) | (Min.:Sec.) |
| 18 | A | 100 | A | 12 | d | 6 | 0.25 | 6:05 | 17:00 |
| 19 | A | 100 | A | 12 | d,l- | 6 | 0.25 | 2:52 | 12:00 |
| 20 | A | 30 | B | 10 | d- | 3 | 0.20 | 9:19 | 180:00 |
| 21 | A | 30 | B | 10 | l- | 3 | 0.20 | 9:55 | 120:00 |
| 22 | A | 30 | B | 10 | d,l- | 3 | 0.20 | 5:16 | 30:00 |
| 23 | B | 30 | B | 10 | d- | 3 | 0.20 | 2:14 | 47:00 |
| 24 | B | 30 | B | 10 | d,l- | 3 | 0.20 | 1:51 | 6:54 |

*by weight

EXAMPLE 2

Figure 2:
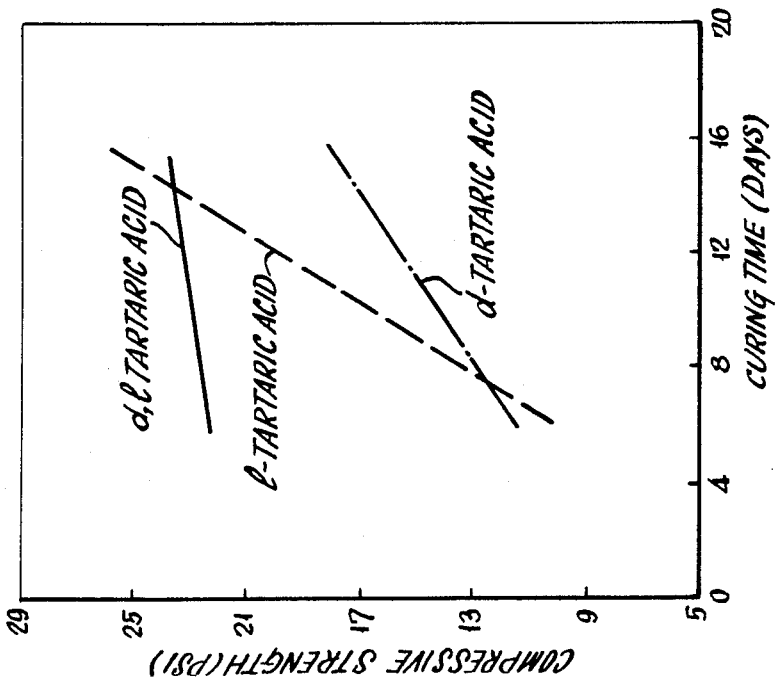
FIG. 2 is a graphical representation, similar to FIG. 1, at a temperature of 100° F.

The compressive strength test described in connection with Example 1 is carried out for a second series of pellets formed from compositions having the same formulation as samples 1, 3, and 4 (using d-, l-, and d,l-isomers of tartaric acid, respectively). These pellets are cured at 70° F. and the compressive strength determined at intervals of several days. Similarly, pellets were cured at 100° F. and 120° F. and tested at intervals of several days. The results are graphically illustrated in FIGS. 1-3. As can be seen from these Figures, the pellets cured at room temperature, i.e., 70° F. exhibit far higher compressive strengths when employing the d,l-isomer form as contrasted with the d- or l-form. There appears to be a tendency for the differences in compressive strengths to lessen as time goes on but even after 36 days the differences are substantial. In contrasting compressive strength data for pellets cured at 70° F. with those cured at 100° and 120° F., respectively, it appears that in the first few days there is a great advantage in employing the d,l-form and that as time passes and as the curing temperature is increased, this advantage diminishes.

EXAMPLE 3

A third series of samples are prepared having the formulations shown in Table 2 wherein the glass and poly(acid) types are those defined in the prior examples. Each of these formulations are tested for "working time" by depositing one gram of homogeneous powdered mixture of the powdered glass, poly(acid) and tartaric acid solids on a watch glass and then adding the specific quantity of water specified in Table 2. A stop watch is started and the powder-water mixture is stirred with a spatula until it reaches a state wherein it is no longer viscous and moldable but instead becomes rubbery and crumbly. At this time, the watch is stopped and the time reported as the "working time" in Table 2.

The same compositions are tested for cure time, at room temperature, using the so-called "Fingernail Test". A mass is made by adding the specified amount of water to one gram of powder mixture and formed into a sphere. The surface of the sphere is scratched with a fingernail and the cure time is measured from the moment of preparation to the point in time when it is no longer possible to gouge a chunk from the surface and when the fingernail no longer leaves a mark on the surface of the sphere.

As can be seen from Table 2, in every case for the spectrum of cementitious compositions, the cure time is greatly accelerated when the d,l-form of tartaric acid is employed. It should also be noted that, notwithstanding the great acceleration in cure times, working times were sufficiently long enough to allow the user to mold the composition to a desired shape.

EXAMPLE 4

The foregoing examples illustrate the advantages of the absolutely optically neutral racemic mixture of d- and l-tartaric acid (d,l-tartaric acid) over either of the two isomers. To illustrate the advantages of mixture of d-, and l- which contain an excess of one of the isomers, samples are prepared using the same formulations as that of samples 1-4 defined in Table 1, with the exception that the tartaric acid employed has various degrees of excess isomer over the racemic mixture. These are defined in Table 3, below and are expressed both as the percent of the d-isomer as well as the percent of racemate mixture.

Compressive strength is determined in accordance with the procedure set out in Example 1 and the results are tabulated in Table 3.

TABLE 3

| | TARTARIC ACID | | COMPRESSIVE STRENGTH |
|---|---|---|---|
| SAMPLE | % d- | % racemate | (kg/cm$^2$) |
| 25 | 100 | 0 | 466.8 |
| 26 | 75 | 50 | 677.1 |
| 27 | 60 | 80 | 739.8 |
| 28 | 50 | 100 | 851.1 |
| 29 | 40 | 80 | 746.8 |
| 30 | 25 | 50 | 636.1 |
| 31 | 0 | 0 | 495.5 |

Figure 4:
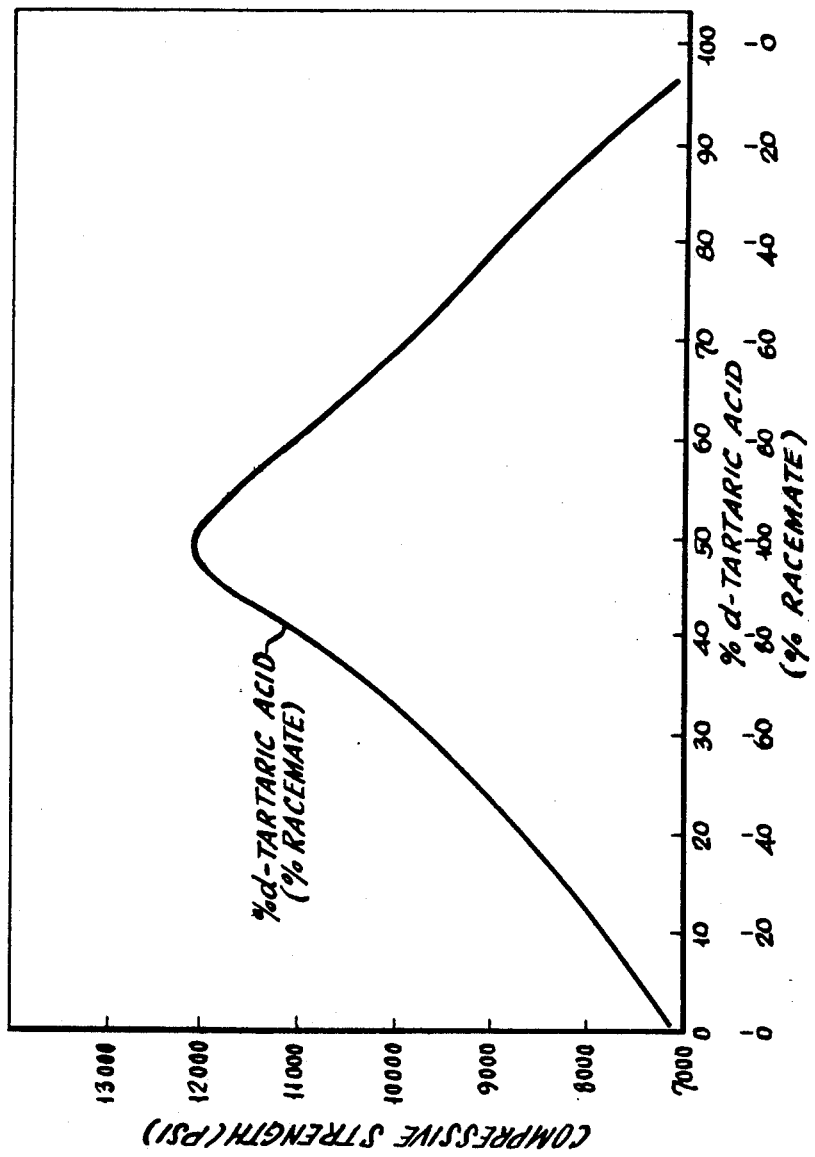
FIG. 4 is a graphical representation illustrating the advantage of utilizing increasing proportions of d,l-tartaric acid.

As can be seen from Table 3, mixtures containing excess isomer still show substantial improvement over those which contain no racemic mixture. In particular mixtures containing up to 75% of either isomer, in combination with the other isomer (i.e., 50% racemate) show such improvement. The results are also illustrated graphically in FIG. 4 wherein a sharp peak in the curve of percent d-isomer vs. compressive strength is noted.

What is claimed is:

1. In a dry cementitious composition comprising ion-leachable glass powder, the improvement wherein said composition further comprises d,l-tartaric acid.

2. The composition of claim 1 wherein said d,l-tartaric acid is present in a quantity of from about 0.05 to about 0.20 grams of d,l-tartaric acid per grams of glass powder.

3. The composition of claim 2 wherein said d,l-tartaric acid is present in a quantity of from about 0.06 to about 0.10 grams of d,l-tartaric acid per gram of glass powder.

4. The composition of claim 1 wherein said dry composition includes excess d-tartaric isomer.

5. The composition of claim 1 wherein said dry composition includes excess l-tartaric isomer.

6. The composition of claim 1 wherein said dry composition includes meso-tartaric acid.

7. The composition of either claim 4, 5 or 6 wherein the d,l-tartaric acid is at least 50% by weight of the total tartaric acid present.

8. The composition of claim 1 further comprising a proton donating compound.

9. The composition of claim 8 wherein said proton donating compound is a poly(carboxylic acid).

10. The composition of claim 9 wherein said poly(carboxylic acid) is poly(acrylic acid).

11. The composition of claim 1 wherein said glass powder is formed from molten inorganic compounds selected from the oxides of alkali, alkaline earth, aluminum and zinc metals and mixtures of these in combination with quartz.

12. The composition of claim 1 in a dental cement.

13. The composition of claim 1 adhered to a bandage substrate.

* * * * *